United States Patent
Liu et al.

(10) Patent No.: US 9,204,950 B2
(45) Date of Patent: Dec. 8, 2015

(54) PLASMA GENERATOR, SURFACE TREATMENT METHOD USING THE SAME AND SURFACE TREATMENT METHOD USING THE SAME FOR BIO-TISSUE

(71) Applicant: INDUSTRIAL TECHNOLOGY RESEARCH INSTITUTE, Hsinchu (TW)

(72) Inventors: Chih-Hung Liu, Taichung (TW); Muh-Wang Liang, Toufen Township, Miaoli County (TW); Shen-Bin Wu, New Taipei (TW); Tean-Mu Shen, Xinpu Township, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 208 days.

(21) Appl. No.: 14/142,598

(22) Filed: Dec. 27, 2013

(65) Prior Publication Data
US 2015/0050614 A1    Feb. 19, 2015

(30) Foreign Application Priority Data

Aug. 16, 2013  (TW) .............................. 102129523 A
Nov. 7, 2013   (TW) .............................. 102140539 A

(51) Int. Cl.
A61C 19/00    (2006.01)
A61B 18/04    (2006.01)
A61C 5/00     (2006.01)

(52) U.S. Cl.
CPC .............. *A61C 19/00* (2013.01); *A61B 18/042* (2013.01); *A61C 5/00* (2013.01)

(58) Field of Classification Search
CPC ......... A61C 19/00; A61C 5/00; A61B 18/042
See application file for complete search history.

(56) References Cited

U.S. PATENT DOCUMENTS

| | | | |
|---|---|---|---|
| 5,225,659 A | 7/1993 | Kusano et al. |
| 6,465,964 B1 | 10/2002 | Taguchi et al. |
| 6,849,306 B2 | 2/2005 | Fukuda et al. |
| 7,064,089 B2 | 6/2006 | Yamazaki et al. |
| 7,307,029 B2 | 12/2007 | Yamazake et al. |
| 7,355,184 B2 | 4/2008 | Nagano |
| 7,456,410 B2 | 11/2008 | Nagano |

(Continued)

FOREIGN PATENT DOCUMENTS

| | | |
|---|---|---|
| CA | 2198622 A1 | 3/1996 |
| CN | 1643642 A | 7/2005 |

(Continued)

OTHER PUBLICATIONS

Y. J., Hong, et al., "Non-thermal atmospheric pressure plasma sources for biomedical applications", Dept. of Physics, Pohang Univ. of Sci. and Tech. (S. Korea), Dept. of Electronic and Electrical Engineering (S. Korea), and Dept. of Oral Anatomy, School of Dentistry (S. Korea), 4 pages.

(Continued)

*Primary Examiner* — Kishor Mayekar
(74) *Attorney, Agent, or Firm* — Muncy, Geissler, Olds & Lowe, P.C.

(57) ABSTRACT

A plasma generator, a surface treatment method using the same, and a surface treatment method using the same for bio-tissue are provided. The plasma generator comprises a plasma tube, a reaction source tube, a first electrode and a second electrode. The plasma tube has a plasma outlet. The reaction source tube is disposed within the plasma tube, and has a reaction outlet. The first electrode and the second electrode are disposed on the plasma tube, wherein the second electrode is closer to the plasma outlet than the first electrode is. The plasma outlet of the reaction source is not projected beyond a lower portion of the first electrode.

23 Claims, 7 Drawing Sheets

(56) References Cited

U.S. PATENT DOCUMENTS

| | | |
|---|---|---|
| 7,462,572 B2 | 12/2008 | Yamazaki et al. |
| 7,642,519 B2 | 1/2010 | Nagano |
| 7,863,577 B2 | 1/2011 | Nagano |
| 8,328,982 B1 | 12/2012 | Babayan et al. |
| 8,338,307 B2 | 12/2012 | De Vries et al. |
| 8,343,786 B2 | 1/2013 | Pyo |
| 2008/0006092 A1 | 1/2008 | Brida et al. |
| 2010/0273129 A1 | 10/2010 | Yu et al. |
| 2011/0183284 A1 | 7/2011 | Yamanaka et al. |
| 2012/0015322 A1 | 1/2012 | Lloyd et al. |
| 2012/0107761 A1 | 5/2012 | Holbeche et al. |
| 2012/0276499 A1 | 11/2012 | Devery et al. |
| 2012/0282574 A1 | 11/2012 | Holbeche |

FOREIGN PATENT DOCUMENTS

| | | |
|---|---|---|
| EP | 1253621 A2 | 10/2002 |
| TW | 200923124 A | 6/2009 |
| TW | I336602 B | 1/2011 |
| TW | 201127354 A | 8/2011 |
| TW | 201210640 A | 3/2012 |
| TW | 201215380 A | 4/2012 |
| TW | I365922 B | 6/2012 |
| TW | 201244761 A | 11/2012 |
| TW | I381827 B | 1/2013 |
| WO | WO2009/128579 A1 | 10/2009 |

OTHER PUBLICATIONS

Provided by Society for General Microbiology, "Painless plasma jets could replace dentist's drill", PHYSorg.com, Jan. 19, 2010, 1 page, http://phys.org/news183153224.html.

Raymond E. J. Sladek, et al., "Plasma Treatment of Dental Cavities: A Feasibility Study", IEEE Transactions on Plasma Science, vol. 32, No. 4, Aug. 2004, pp. 1540-1543.

Hyun Woo Lee, et al., "Tooth Bleaching with Nonthermal Atmospheric Pressure Plasma", JOE, vol. 35, No. 4, Apr. 2009, pp. 587-591.

Hyun Woo Lee, et al., "Atmospheric Pressure Plasma Jet Composed of Three Electrodes: Application to Tooth Bleaching", Plasma Process. Polym, vol. 7, 2010, pp. 274-280.

Gan Young Park, et al., :Biomedical Applications of Low Temperature Atmospheric Pressure Plasmas to Cancerous Cell Treatment and Tooth Bleaching, Inst. of Heath Sci. Biomedical Center (Rep. of Korea), Dept. of Oral Maxillofacial Surgery (Rep. of Korea), Dept. of Electronic and Electrical Engineering (Rep. of Korea), Dept. of Life Sci., Div. of Molecular and Life Sci. (Rep. of Korea), and Dept. of Oral Anatomy, School of Dentistry (Rep. of Korea), 4 pages.

Myoung Soo Kim, et al., "Correlated Electrical and Optical Studies of Hybrid Argon Gas-Water Plasmas and Their Application to Tooth Whitening", Plasma Process. Polym, vol. 9, 2012, pp. 339-345.

Stefan Rupf, et al., "Killing of adherent oral microbes by a nonthermal atmospheric plasma jet", Journal of Medical Microbiology, vol. 59, 2010, pp. 206-212.

H. W., Lee, et al., "Modelling of atmospheric pressure plasmas for biomedical applications", J. Phys. D: Appl. Phys, vol. 44, 2011, pp. 1-27.

Gan Young Park, et al., Biomedical Applications of Low Temperature Atmospheric Pressure Plasmas to Cancerous Cell Treatment and Tooth Bleaching, Japanese Journal of Applied Physics 50, Aug. 22, 2011, pp. 1-4.

Hong, Y.J. et al., Non-thermal atmospheric pressure plasma for biomedical applications, 2012 Plasma Sources Science Technology, Jun. 2012, pp. 1-4.

PLASMA GENERATOR, SURFACE TREATMENT METHOD USING THE SAME AND SURFACE TREATMENT METHOD USING THE SAME FOR BIO-TISSUE

This application claims the benefit of Taiwan application Serial No. 102129523, filed Aug. 16, 2013, and the benefit of Taiwan application Serial No. 102140539, filed Nov. 7, 2013, the disclosure of which are incorporated by reference herein in its entirety.

TECHNICAL FIELD

The disclosure relates in general to a plasma generator, a surface treatment method using the same and a surface treatment method using the same for bio-tissue, and more particularly to a plasma generator with a tube, a surface treatment method using the same and a surface treatment method using the same for bio-tissue.

BACKGROUND

Normally, a decayed tooth is filled up without applying a pre-treatment of sterilization, therefore bacteria residue may be left during the filling process, and make the filling material come off easily. In some cases, a pre-treatment of sterilization is applied to biological tissues. However, ordinary sterilization process still cannot effectively kill bacteria.

SUMMARY

According to one embodiment, a plasma generator is provided. The plasma generator comprises a plasma tube, a reaction source tube, a first electrode and a second electrode. The plasma tube has a plasma outlet. The reaction source tube is disposed within the plasma tube, and has a reaction outlet. The first electrode is disposed on the plasma tube. The second electrode is disposed on the plasma tube and is closer to the plasma outlet of the plasma tube than the first electrode is. The plasma outlet of the reaction source is not projected beyond a lower portion of the first electrode.

According to another embodiment, a surface treatment method is provided. The surface treatment method comprises following steps. Firstly, a plasma generator is provided, wherein the plasma generator comprises a plasma tube, a reaction source tube, a first electrode and a second electrode. The plasma tube has a plasma outlet. The reaction source tube is disposed within the plasma tube, and has a reaction outlet. The first electrode is disposed on the plasma tube. The second electrode is disposed on the plasma tube, and is closer to the plasma outlet of the plasma tube than the first electrode is. The plasma outlet of the reaction source is not projected beyond a lower portion of the first electrode. Next, a plasma source gas within the plasma tube is excited by the first electrode and the second electrode to generate plasma. Lastly, a reactant is provided to the plasma from the reaction source tube, and is further decomposed by the plasma to generate a surface treatment element for performing surface treatment on a to-be-processed object.

According to an alternative embodiment, a surface treatment method for bio-tissue is provided. The surface treatment method for a tooth comprises following steps. Firstly, a plasma generator is provided, wherein the plasma generator comprises a plasma tube, a reaction source tube, a first electrode and a second electrode. The plasma tube has a plasma outlet. The reaction source tube is disposed within the plasma tube, and has a reaction outlet. The first electrode is disposed on the plasma tube. The second electrode is disposed on the plasma tube and is closer to the plasma outlet of the plasma tube than the first electrode is. The plasma outlet of the reaction source is not projected beyond a lower portion of the first electrode. Next, a plasma source gas within the plasma tube is excited by the first electrode and the second electrode to generate plasma for performing a first surface treatment on the bio-tissue.

The above and other aspects of the disclosure will become better understood with regard to the following detailed description of the preferred but non-limiting embodiment(s). The following description is made with reference to the accompanying drawings.

Figure 1A:
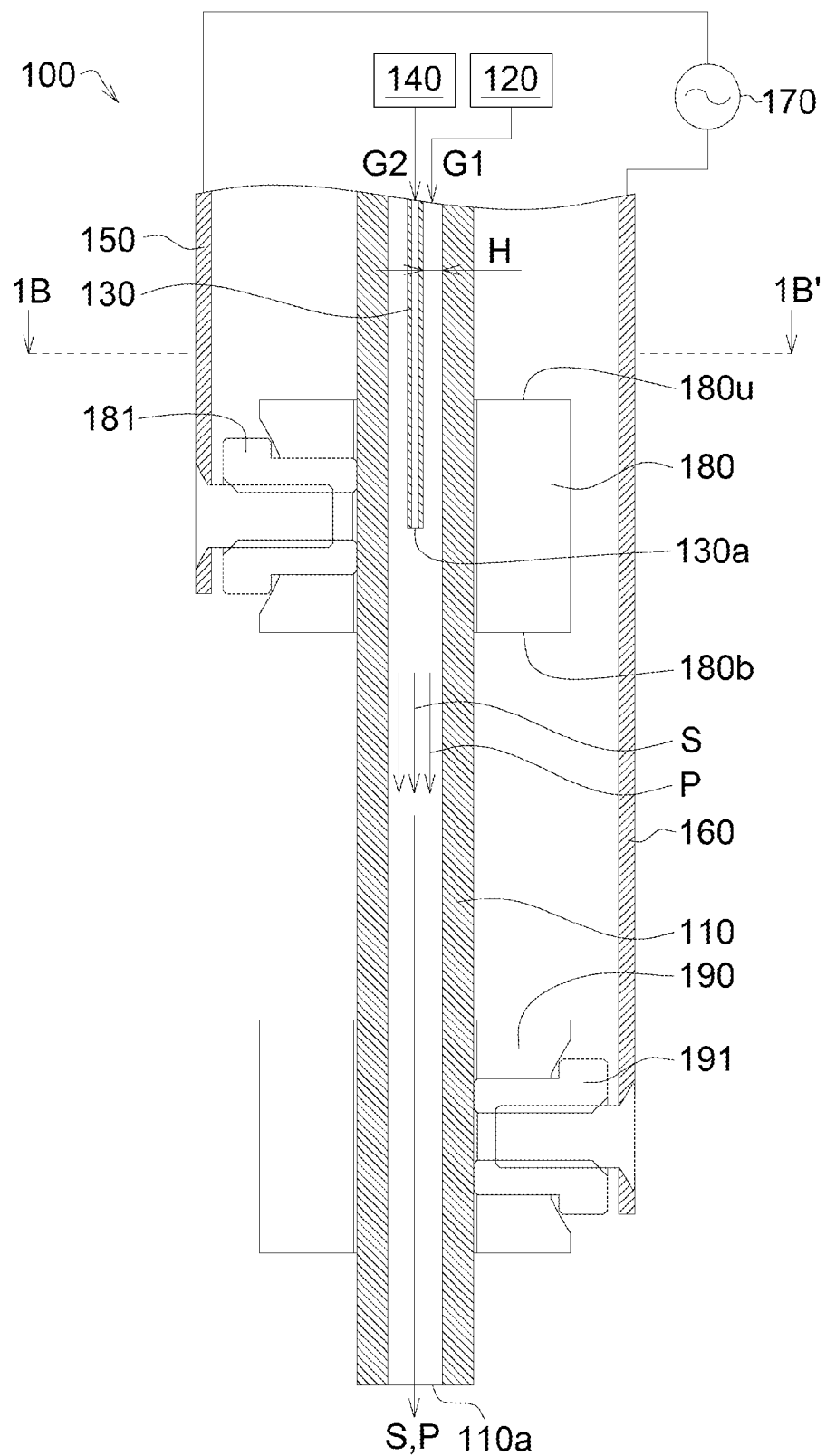
FIG. 1A shows a cross-sectional view of a plasma generator according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Referring to FIG. 1A, a cross-sectional view of a plasma generator according to an embodiment of the disclosure is shown. The plasma generator 100 has a small volume and can thus be held in hand. The plasma generator 100 can such as whiten, repair or sterilize on a tooth or several teeth whether inside or outside the oral cavity, skin or other tissues. In an embodiment, the plasma generator 100 performs sterilizing and repairing the tooth (such as a decayed tooth) inside the oral cavity. For the tooth outside the oral cavity, the plasma generator 100 performs a surface treatment on the tooth and afterwards the tooth is implanted into the oral cavity. The object of surface treatment is not limited to the tooth. For example, the plasma generator 100 can also perform surface treatment on skin or other biological tissues.

The plasma generator 100 comprises a plasma tube 110, a plasma gas source 120, a reaction source tube 130, a reactant source 140, a first conductive sheet 150, a second conductive sheet 160, a power supply unit 170, a first electrode 180 and a second electrode 190.

The plasma tube 110 interconnects with the plasma gas source 120, which provides a plasma source gas G1 to the plasma tube 110. When the plasma source gas G1 passes through the area between the first electrode 180 and the second electrode 190, the plasma source gas G1 will be excited to generate a plasma P. Then, the plasma P is ejected from the plasma outlet 110a of the plasma tube 110 to perform surface treatment, such as sterilization, on a biological tissue to avoid the biological tissue being infected. The plasma tube 110 can have an outer diameter less than 20 millimeters. In the present embodiment, the plasma tube 110 is an insulating plasma tube. In an embodiment, a distance between the plasma outlet 110a and the treated bio-tissue can be larger than 1 millimeter.

The reaction source tube 130 interconnects with the reactant source 140 which provides a reactant G2 to the reaction source tube 130. After the plasma P is generated, the reactant G2 is mixed with the plasma P and is further decomposed by the plasma P to generate a surface treatment element S. The surface treatment element S is such as an element for whitening the tooth or a bio-compatible element for repairing a tissue. Suppose the reactant G2 is water vapor (liquid mist). After the water vapor is mixed with the plasma P, the water vapor is decomposed by the plasma P to generate a surface treatment element S, such as an oxygen radical and a hydroxyl radical, which removes pigments off the surface of the tooth and achieves the tooth whitening effect. Also, during the process of decomposing the water vapor by the plasma P, the temperature of surface treatment will drop. Under such circumstance, the oxidation of the tooth will slow down, hence benefiting the whitening of the tooth. With suitable control, the temperature of surface treatment can be controlled to be closer to that of the biological tissue. For the human body, the temperature of surface treatment can be controlled to be lower than 40 degrees Celsius.

Suppose the reactant G2 is liquid hydroxylapatite $Ca_5(PO_4)_3(OH)$. After hydroxylapatite and the plasma P are mixed, hydroxylapatite is decomposed by the plasma P to generate a bio-compactible material capable of repairing a biological tissue (such as the tooth, skin or other biological tissues) and helping the biological tissue to recover faster. In terms of properties, hydroxylapatite is non-toxic and decomposable, exists in the bone and tooth of the human body, and is an ingredient for forming calcium. However, the variety of reactant G2 is not restricted in the embodiment of the disclosure, and any reactants which are decomposed by the plasma P and capable of generating a surface treatment element used for repairing biological tissues, killing or suppressing bacteria and/or used for cosmetics purpose can be used as the reactant G2.

In the present embodiment, the reaction source tube 130 is an insulating plasma tube, and will not generate any electricity affecting the generation of the plasma P. In another embodiment, the reaction source tube 130 and the plasma tube 110 are disposed in a concentric manner, such that the radial spacing H between the reaction source tube 130 and the plasma tube 110 is basically the same. Therefore, the flow velocity of the plasma source gas G1 passing through the radial spacing H is even more uniform, and the uniformity of the flow velocity of the generated plasma P is further improved.

The reaction source tube 130 has a reaction outlet 130a via which the reactant G2 inside the reaction source tube 130 is provided to the plasma P. The reaction outlet 130a is not projected beyond a lower portion of the first electrode 180, but is located such as between an upper surface 180u and a lower surface 180b of the first electrode 180.

The first conductive sheet 150 is extended to a first polarity terminal of the power supply unit 170 from the first electrode 180, and the second conductive sheet 160 is extended to a second polarity terminal of the power supply unit 170 from the second electrode 190. The power supply unit 170 provides a radio frequency (RF) power to the first electrode 180 and the second electrode 190 through the first conductive sheet 150 and the second conductive sheet 160 to excite the plasma source gas G1 to generate the plasma P. The first conductive sheet 150 and the second conductive sheet 160 can be formed by metal or graphite in the form of a plate to enhance the structural strength of the plasma generator 100 and make the plasma generator 100 easier to be held in hand. In another embodiment, the first conductive sheet 150 and the second conductive sheet 160 can be replaced with wires.

The first electrode 180 comprises a first protrusion 181 pressing an outer wall of the plasma tube 110. Likewise, the second electrode 190 comprises a second protrusion 191 pressing an outer wall of the plasma tube 110. With the first protrusion 181 and the second protrusion 191 pressing two opposite outer walls of the plasma tube 110, relative positions between the plasma tube 110 and two electrodes (180 and 190) can be fixed.

Figure 1B:
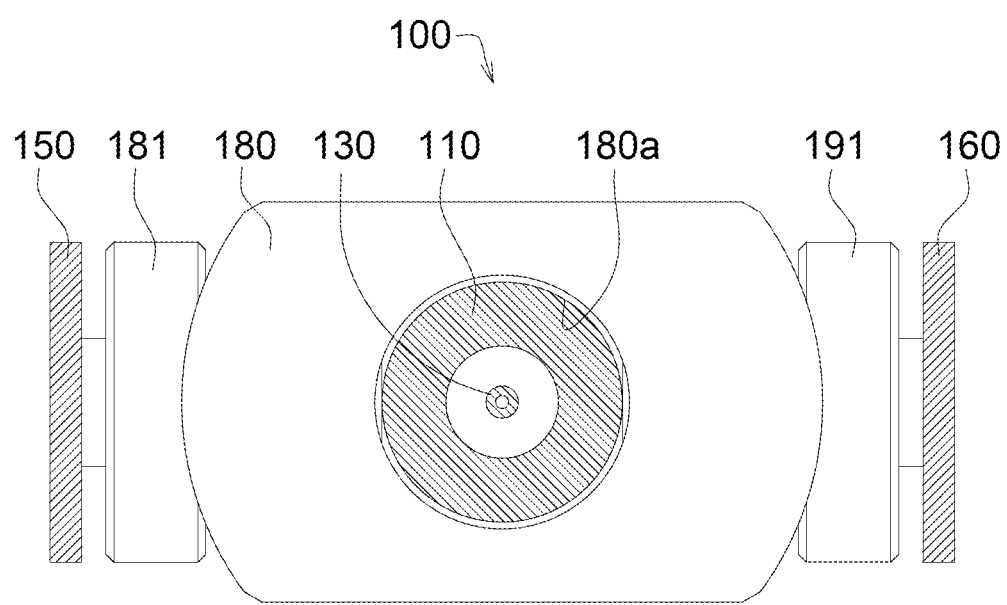
FIG. 1B shows a cross-sectional view along a cross-sectional direction 1B-1B' of FIG. 1A.

Referring to FIG. 1B, a cross-sectional view along a cross-sectional direction 1B-1B' of FIG. 1A is shown. The first electrode 180 is a ring-shaped electrode having via hole 180a through which the plasma tube 110 passes. In another embodiment, the via hole 180a and the plasma tube 110 can be tightly disposed to fix their relative position. Under such design, the first protrusion 181 and the second protrusion 191 do not have to press the outer walls of the plasma tube 110. Besides, the structure of the second electrode 190 is similar to that of the first electrode 180, and the similarities are not repeated here.

Figure 2A:
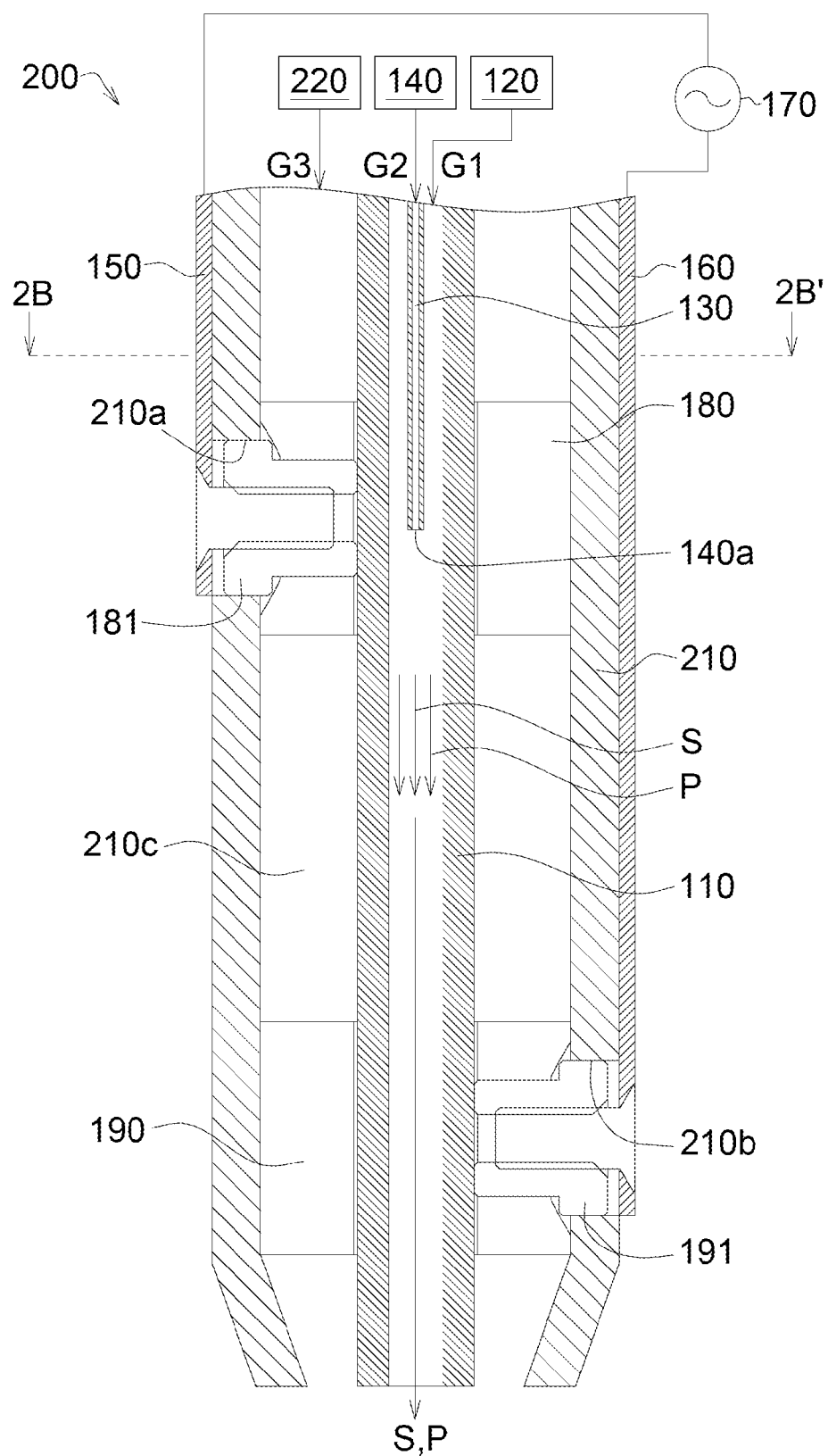
FIG. 2A shows a cross-sectional view of a plasma generator according to another embodiment of the disclosure.

Referring to FIG. 2A, a cross-sectional view of a plasma generator according to another embodiment of the disclosure is shown. The plasma generator 200 comprises the plasma tube 110, the plasma gas source 120, the reaction source tube 130, the reactant source 140, the first conductive sheet 150, the second conductive sheet 160, the power supply unit 170, the first electrode 180, the second electrode 190, a cooling tube 210 and a cooling source 220.

The cooling tube 210 encapsulates the plasma tube 110, the first electrode 180 and the second electrode 190. A cooling cavity 210c is defined between the cooling tube 210 and the plasma tube 110. The first electrode 180 and the second electrode 190 are located inside the cooling cavity 210c. The cooling source 220 provides a cooling agent G3 to the cooling tube 210 to lower the temperature of the first electrode 180 and the second electrode 190 inside the cooling cavity 210c to avoid the oxidization of the first electrode 180 and the second electrode 190 being expedited due to high temperature. Besides, the cooling agent G3 also lowers the temperature of the plasma P and the surface treatment element S to benefit the whitening of the tooth. Since the cooling tube 210 has an insulating property, the generation of the plasma P will not be affected even when the cooling tube 210 contacts the first electrode 180 and the second electrode 190.

Figure 2B:
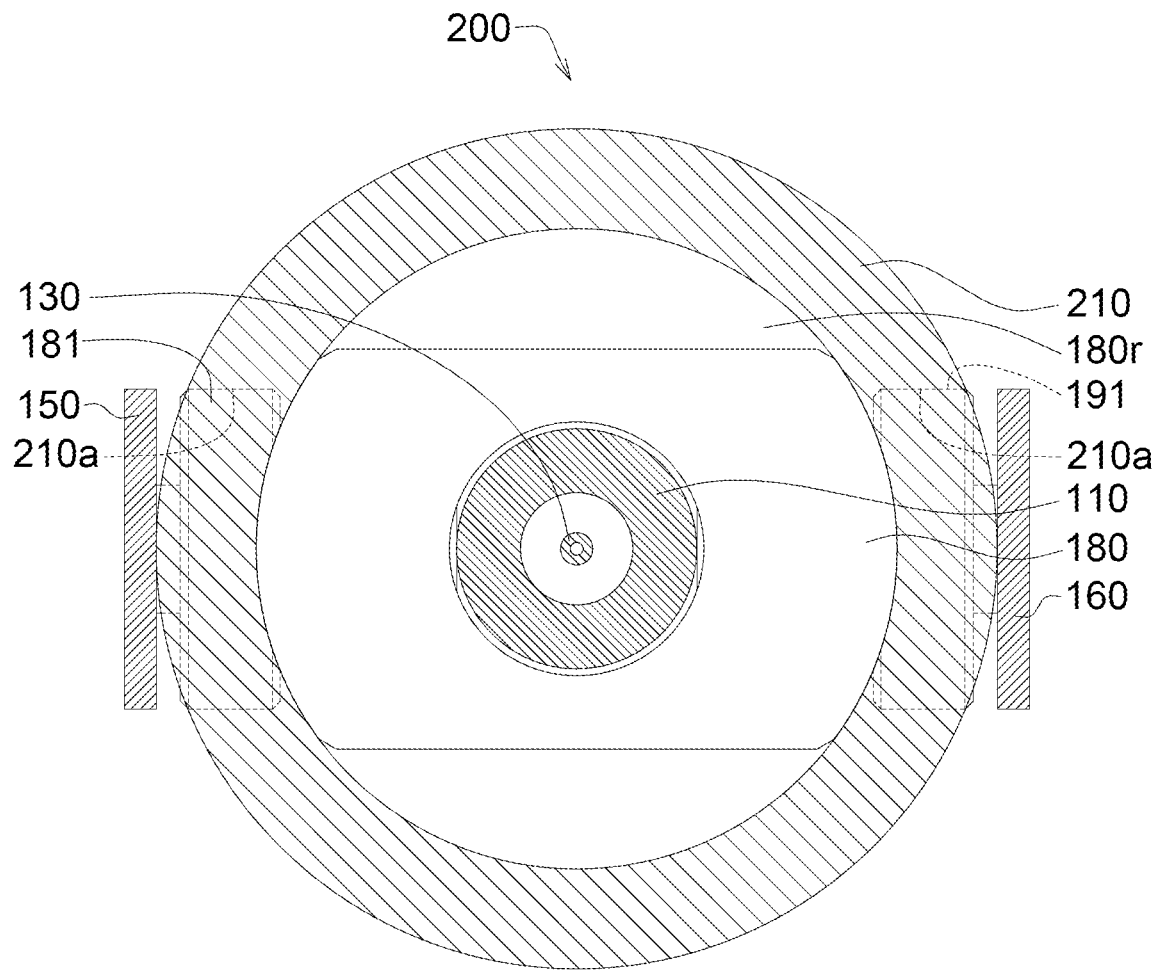
FIG. 2B shows a cross-sectional view along a cross-sectional direction 2B-2B' of FIG. 2A.

Referring to FIG. 2B, a cross-sectional view along a cross-sectional direction 2B-2B' of FIG. 2A is shown. The first electrode 180 has an opening 180r interconnecting with the cooling cavity 210c (not illustrated in FIG. 2B) for allowing the cooling agent G3 (not illustrated in FIG. 2B) to pass through. In the present embodiment, the opening 180r is a gap which can be formed by hollowing a conductive lump with a circular cross-section. The hollowed part will form the opening 180r which is a via hole penetrating the entire thickness of the first electrode 180.

The cooling tube 210 has a first through hole 210a (also illustrated in FIG. 2A). The first protrusion 181 is disposed within the first through hole 210a and exposed from the first through hole 210a, such that the first conductive sheet 150 is electrically connected to the first electrode 180 through the first protrusion 181. Likewise, the cooling tube 210 has a second through hole 210b (illustrated in FIG. 2A). The second protrusion 191 is disposed within the second through hole 210b and exposed from the second through hole 210b, such that the second conductive sheet 160 is electrically connected to the second electrode 190 (illustrated in FIG. 2A) through the second protrusion 191.

Figure 3A:
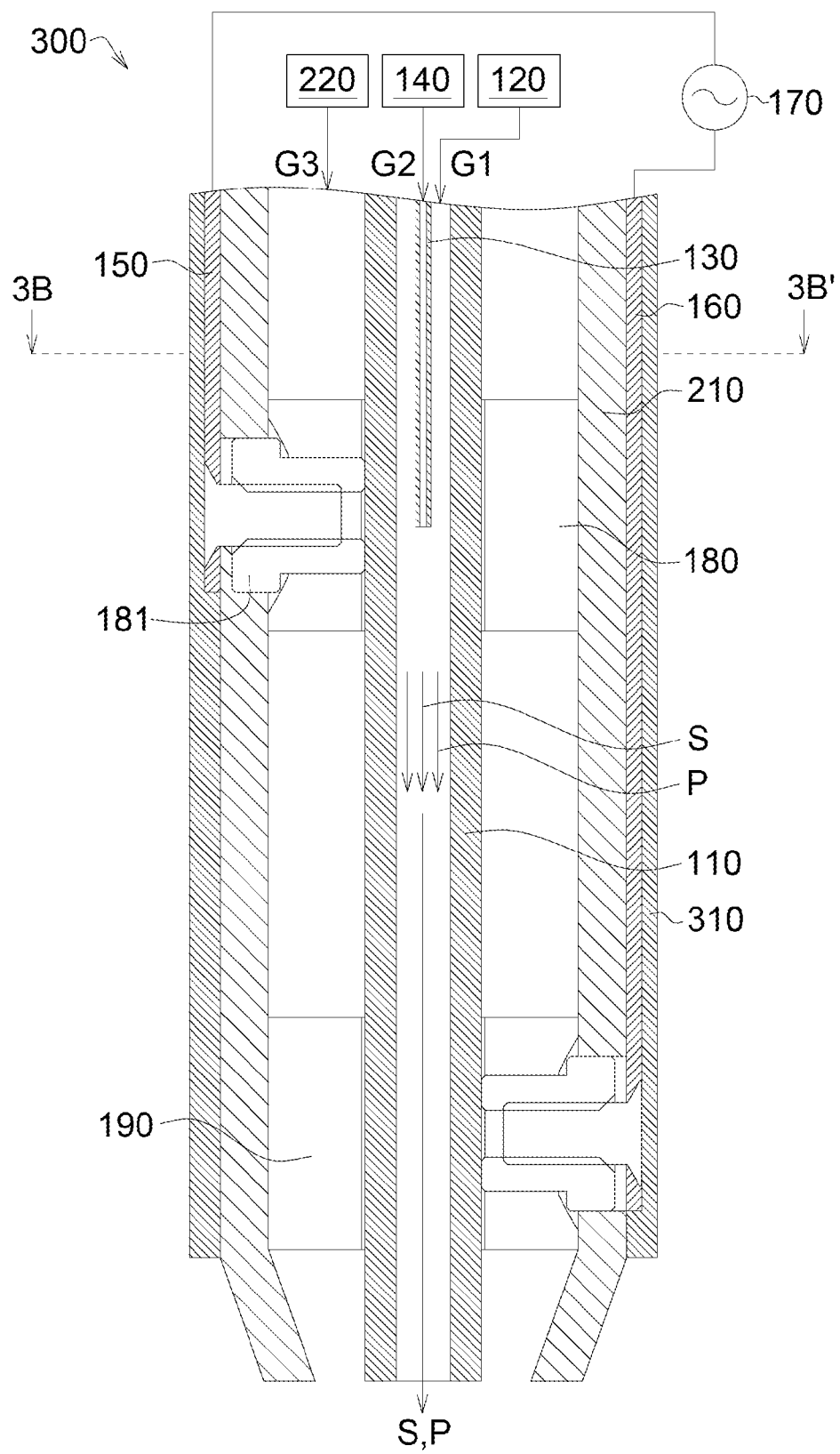
FIG. 3A shows a cross-sectional view of a plasma generator according to an alternate embodiment of the disclosure.

Referring to FIG. 3A, a cross-sectional view of a plasma generator according to an alternate embodiment of the disclosure is shown. The plasma generator 300 comprises the plasma tube 110, the plasma gas source 120, the reaction source tube 130, the reactant source 140, the first conductive sheet 150, the second conductive sheet 160, the power supply unit 170, the first electrode 180, the second electrode 190, the cooling tube 210, the cooling source 220 and a protection tube 310. The protection tube 310 encapsulates the cooling tube 210. In addition, the protection tube 310 also encapsulates the first protrusion 181 and the second protrusion 191.

Figure 3B:
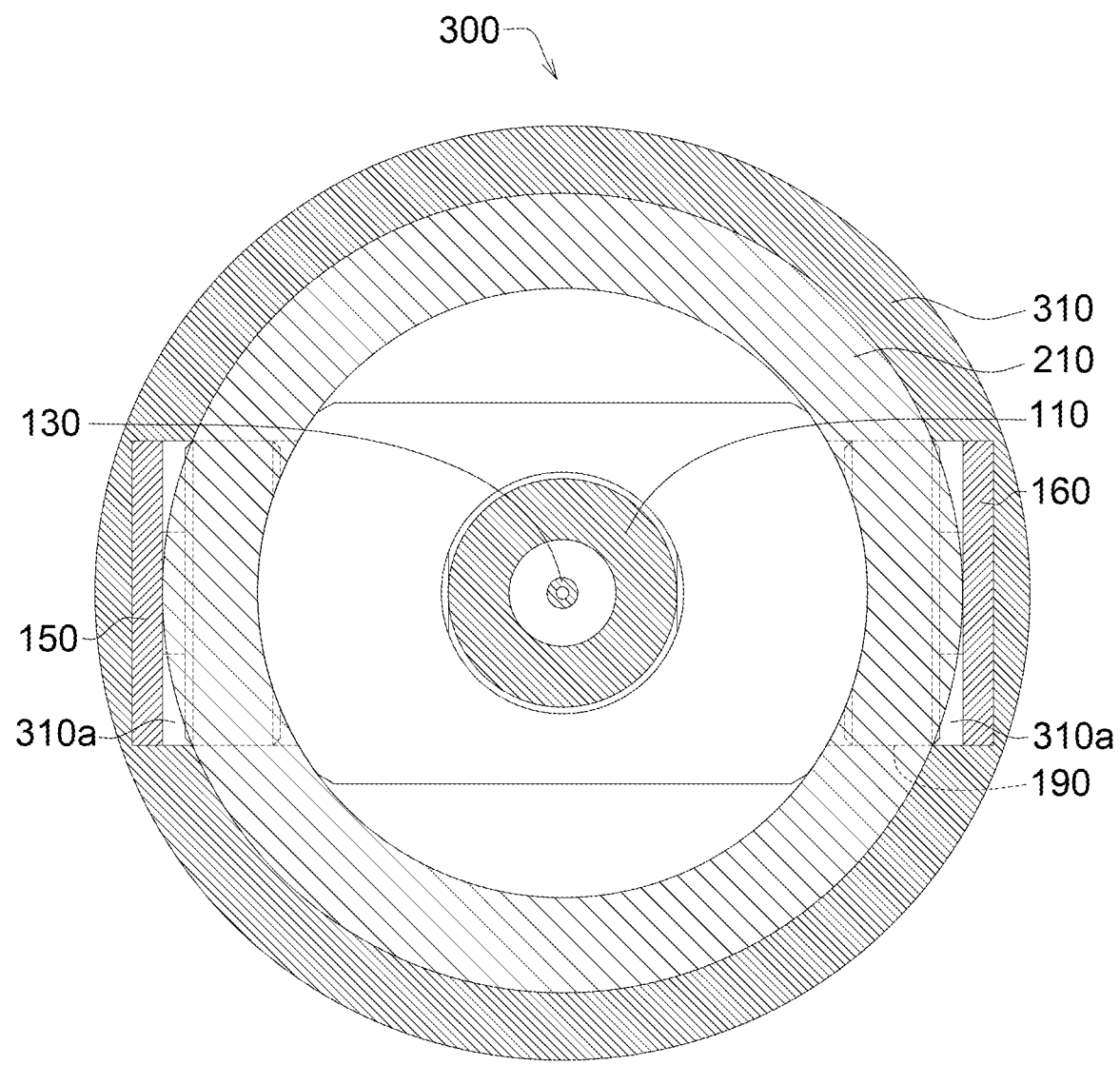
FIG. 3B shows a cross-sectional view along a cross-sectional direction 3B-3B' of FIG. 3A.

Referring to FIG. 3B, a cross-sectional view along a cross-sectional direction 3B-3B' of FIG. 3A is shown. The protection tube 310 has a depressed portion 310a engaged with the first conductive sheet 150 and the second conductive sheet 160.

Figure 4:
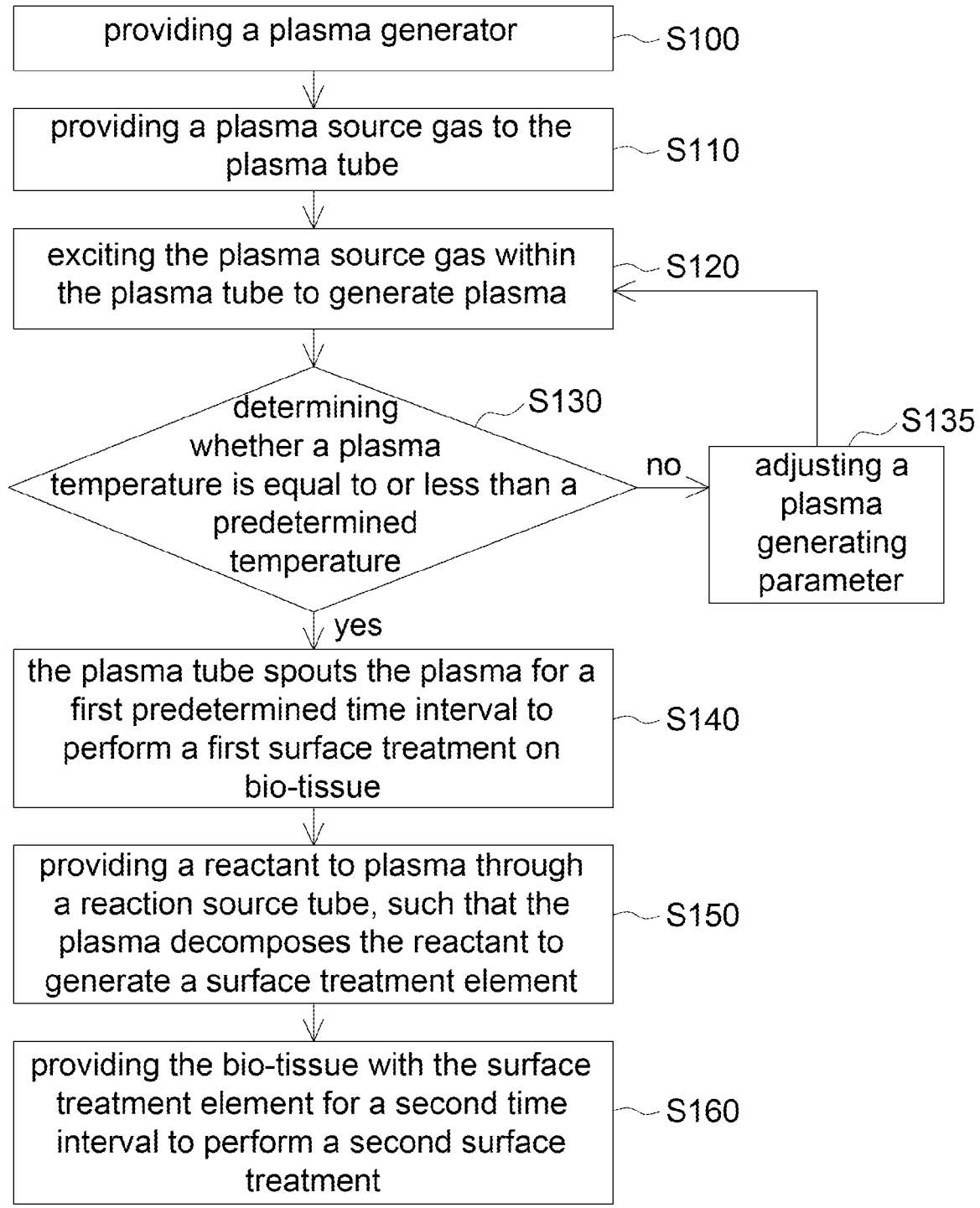
FIG. 4 shows a flow chart of using plasma generator to perform a surface treatment on bio-tissue according to an embodiment of the disclosure.

Referring to FIG. 4, a flow chart of using plasma generator to perform a surface treatment on bio-tissue according to an embodiment of the disclosure is shown. The above plasma generator 100 can perform surface treatment, such as sterilizing, whitening, deallergization, repairing, bacteriostasis or other treatment for bio-tissue, such as the tooth in oral cavity, the tooth outside oral cavity (a artificial tooth, for example), skin or other tissue. In an embodiment, the plasma generator 100 can sterilize or repair the tooth (a decayed tooth, for example) in oral cavity. Alternatively, the plasma generator 100 can perform surface treatment on the tooth outside oral cavity, and then the treated tooth is implanted in oral cavity. In addition, the plasma generator 100 can perform surface treatment on not only the tooth but also skin or other tissues.

In step S100, the plasma generator 100 or 200 is provided. The plasma generator 100 of FIG. 1A is taken for example.

In step S110, as illustrated FIG. 1A, the plasma source gas G1 is provided to the plasma tube 110. The plasma source gas G1 may be air, argon, helium, oxygen or nitrogen.

In step S120, as illustrated in FIG. 1A, the plasma source gas G1 within the plasma tube 110 is excited to generate plasma P. In an embodiment, the RF power is provided by the power supply unit 170 to excite the plasma source gas G1 to generate plasma P.

In step S130, the plasma generator 100 determines whether plasma temperature is equal to or less than a predetermined temperature. If the plasma temperature is larger than the predetermined temperature, step S135 is performed. If the plasma temperature is less than or equal to the predetermined temperature, step S140 is performed. The predetermined temperature is an appropriate temperature for to-be-treated bio-tissue, such as about 40 degrees centigrade. In an embodiment, the plasma generator 100 is selectively comprises a temperature sensor for sensing a temperature of the generated plasma, wherein the temperature sensor is a thermometer, thermocouple or thermal paper.

In step S135, when the plasma temperature is larger than the predetermined temperature, the plasma generator 100 can automatically adjust a plasma generating parameter to reduce plasma temperature. The plasma generating parameter may be quantity of flow of the plasma source gas G1, current value of the power supply unit 170, power of the power supply unit 170, rate of pulse duration of the power supply unit 170 or other appropriate parameter. In an embodiment, the plasma temperature can be reduced to less than the predetermined temperature by adjusting one of quantity of flow of the plasma source gas G1, current value of the power supply unit 170, power of the power supply unit 170, and rate of pulse duration, or a combination thereof.

In step S140, when the plasma generating temperature is less than or equal to the predetermined temperature, the plasma outlet 110a of the plasma tube 110 can spout plasma P for a first predetermined time interval to perform a first surface treatment on bio-tissue. The first surface treatment is sterilization, for example. The first predetermined time interval is 20 seconds, less than 20 seconds or more than 20 seconds, for example. In an embodiment, a distance between the plasma outlet 110a and the bio-tissue is larger than 1 millimeter.

In the present embodiment, other surface treatment can be performed for bio-tissue in step S150. In another embodiment, the step S150 and S160 can be omitted.

In step S150, the reactant G2 can be provided through the reaction source tube 130, such that the plasma P decomposes the reactant G2 to generate the surface treatment element S. The reactant G2 is water vapor, hydroxylapatite, fluoride, fluorosilicone monomer, tetraethoxysilane ($Si(OC_2H_5)_4$), titanium isopropoxide (($CH_3CH_3CHO)_4Ti$) or methane.

In step S160, the bio-tissue is provided with the surface treatment element S for a second time interval to perform a second surface treatment. The reactant G2 is decomposed by the plasma P to generate a surface active element. After the surface active element is reacted with the bio-tissue, surface treatment for helping bio-tissue to repair, recover and/or making cosmetic can be realized. When the reactant G2 is water vapor (liquid mist) or air with water vapor, the second surface treatment may be whitening treatment on bio-tissue. When the reactant G2 is hydroxylapatite or methane, the second surface treatment may generate a surface material with biocompatibility. When the reactant G2 is fluoride, the second surface treatment may prevent the tooth from being decayed. When the reactant G2 is fluorosilicone monomer, tetraethoxysilane, ortitanium isopropoxide, the second surface treatment can be desensitizing treatment for repairing uncovered dentinal tubule. The second time interval may be 30 seconds, more than 30 seconds or less than 30 seconds, for example.

The surface treatment method for bio-tissue is provided in the present disclosure. During the method, the plasma source gas is excited to generate the plasma having a plasma temperature not larger than a temperature appropriate to bio-tissue to perform surface treatment, such as sterilization, whitening, desensitization, reparation, bacteriostasis or other treatment, by adjusting plasma generating parameter. Ozone generated by plasma can perform a variety of sterilization. After sterilization is performed for a predetermined time interval, the reactant can be provided for decomposing plasma to generate the surface active treatment element. Such surface active treatment element has biocompatibility and capable of whitening or repairing bio-tissue. When the reactant G2 is water vapor (liquid mist), the plasma decomposes the water vapor to generate the surface treatment element, such as oxide radical and hydroxyl radical, to remove pigment on the tooth for whitening. When the reactant G2 is liquid hydroxylapatite, the plasma decomposes calcium hydroxylapatite to generate biocompatibility material to repair bio-tissue (for example, the tooth, skin or other bio-tissue) for expediting recover of bio-tissue. When the reactant is fluoride, based on excellent affinity between fluorine and calcium, hydroxylapatite on enamel can be converted to calcium fluoroapatite with low solubility, such that solubility of enamel in acid can be reduced. In addition, after the fluorine is calcified and combined with calcium, the fluorine returns the interior of the tooth. As a result, progress of early decayed tooth is reversed, speed of causing decayed tooth is reduced, and thus the advantage of preventing from decayed tooth is realized. The above reactant is not restricted to above embodiment. As long as a material can be decomposed to generate the surface treatment element conducive to revivification, regeneration, reparation or whitening for bio-tissue, such material can be the reactant of the disclosure.

The surface treatment disclosed in above disclosure is not restricted to affected part of bio-tissue. The surface treatment of the present disclosure also may be suitable for healthy bio-tissue, such as healthy skin, the tooth, other bio-tissue, or abiotic substance. Particularly, the surface treatment for the tooth can be a surface treatment for not only an affected tooth of patient, but also a healthy tooth for whitening or health care, for example.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A plasma generator, comprising:
   a plasma tube having a plasma outlet;
   a reaction source tube disposed within the plasma tube and having a reaction outlet;
   a first electrode disposed on the plasma tube and having a lower surface towards the plasma outlet; and
   a second electrode disposed on the plasma tube and closer to the plasma outlet of the plasma tube than the first electrode is;
   wherein the reaction outlet of the reaction source tube is not projected beyond the lower surface of the first electrode.

2. The plasma generator according to claim 1, further comprising:
   a reactant source providing a reactant to the reaction source tube.

3. The plasma generator according to claim 2, wherein the reactant is water vapor, air with water vapor, hydroxylapatite, fluoride, fluorosilicone monomer, tetraethoxysilane, titanium isopropoxide or methane.

4. The plasma generator according to claim 1, wherein the reaction outlet of the reaction source tube is located between an upper surface of the first electrode and the lower surface of the first electrode.

5. The plasma generator according to claim 1, further comprising:
   a first conductive sheet electrically connecting the first electrode and a first polarity terminal of a power supply unit; and
   a second conductive sheet electrically connecting the second electrode and a second polarity terminal of the power supply unit.

6. The plasma generator according to claim 1, wherein each of the first electrode and the second electrode is a ring-shaped electrode, and each ring-shaped electrode has a through hole through which the plasma tube passes.

7. The plasma generator according to claim 1, further comprising:
   a cooling tube within which the plasma tube is disposed, wherein a cooling cavity is defined between the cooling tube and the plasma tube, and the first electrode and the second electrode are located within the cooling cavity.

8. The plasma generator according to claim 7, wherein the first electrode has an opening interconnecting with the interior of the cooling tube for allowing the cooling agent to pass through.

9. The plasma generator according to claim 7, wherein the first electrode comprises a first protrusion, the cooling tube has a first through hole, the first protrusion is disposed within the first through hole and exposed from the first through hole, and the plasma generator further comprises:
   a first conductive sheet electrically connected to the first electrode through the first protrusion.

10. The plasma generator according to claim 7, wherein the second electrode comprises a second protrusion, the cooling tube has a second through hole, the second protrusion is disposed within the second through hole and exposed from the second through hole, and the plasma generator further comprises:
    a second conductive sheet electrically connected to the second electrode through the second protrusion.

11. The plasma generator according to claim 1, wherein the plasma tube and the reaction source tube are configured in a concentric manner.

12. A surface treatment method, comprising:
    providing a plasma generator according to claim 1;
    exciting a plasma source gas within the plasma tube by the first electrode and the second electrode to generate plasma; and
    providing a reactant to the plasma from the reaction source tube, wherein the reactant is decomposed by the plasma to generate a surface treatment element for performing surface treatment on a to-be-processed object.

13. The surface treatment method according to claim 12, wherein the to-be-processed object is a biological tissue.

14. A surface treatment method for bio-tissue, comprising:
    providing a plasma generator comprising a plasma tube, a reaction source tube, a first electrode and a second electrode; the plasma tube has a plasma outlet; the reaction source tube is disposed within the plasma tube, and has a reaction outlet; the first electrode and the second electrode are disposed on the plasma tube, wherein the first electrode has a lower surface towards the plasma outlet, and wherein the second electrode is closer to the plasma outlet than the first electrode is;
    the reaction outlet of the reaction source tube is not projected beyond the lower surface of the first electrode; and
    exciting a plasma source gas within the plasma tube by the first electrode and the second electrode to generate plasma for performing a first surface treatment on the bio-tissue.

15. The surface treatment method for the bio-tissue according to claim 14, further comprising:
    determining whether a temperature of the plasma is equal to or less than a predetermined temperature;
    if the temperature of the plasma is equal to or less than the predetermined temperature, performing the first surface treatment on the bio-tissue; and
    if the temperature of the plasma is larger than the predetermined temperature, adjusting a plasma generating parameter, such that the temperature of the plasma is equal to or less than the predetermined temperature.

16. The surface treatment method for the bio-tissue according to claim 15, wherein plasma generating parameter is one of quantity of flow of the plasma source gas, current value of a power supply unit, power of the power supply unit, rate of pulse duration of the power supply unit or combination thereof.

17. The surface treatment method for the bio-tissue according to claim 14, further comprising:
    providing the plasma to perform the first surface treatment on the bio-tissue for a first predetermined time interval.

18. The surface treatment method for the bio-tissue according to claim 14, further comprising:

providing a reactant to the plasma through the reaction source tube, such that the plasma decomposes the reactant to generate a surface treatment element for performing a second surface treatment on the bio-tissue.

19. The surface treatment method for the bio-tissue according to claim 14, wherein the step of exciting the plasma source gas within the plasma tube by the first electrode and the second electrode to generate the plasma comprises:

providing a radio frequency (RF) power to the first electrode and the second electrode by a power supply unit to excite the plasma source gas within the plasma tube.

20. The surface treatment method for the bio-tissue according to claim 19, wherein the plasma generator further comprises:

a first conductive sheet electrically connecting the first electrode and a first polarity terminal of the power supply unit; and a second conductive sheet electrically connecting the second electrode and a second polarity terminal of the power supply unit.

21. The surface treatment method for the bio-tissue according to claim 14, wherein the plasma source gas is air, argon, helium, oxygen or nitrogen.

22. The surface treatment method for the bio-tissue according to claim 18, wherein the reactant is water vapor, air with water vapor, hydroxylapatite, fluoride, fluorosilicone monomer, tetraethoxysilane, titanium isopropoxide or methane.

23. The surface treatment method for the bio-tissue according to claim 14, wherein the reaction outlet of the reaction source tube is located between an upper surface and the lower surface of the first electrode.

* * * * *